US008425525B2

(12) United States Patent  
Baumgart

(10) Patent No.: US 8,425,525 B2  
(45) Date of Patent: Apr. 23, 2013

(54) INSTRUMENT SET FOR MINIMALLY INVASIVE PREPARATION FOR BONE NAILING

(76) Inventor: Rainer Baumgart, München (DE)

( * ) Notice: Subject to any disclaimer, the term of this patent is extended or adjusted under 35 U.S.C. 154(b) by 939 days.

(21) Appl. No.: 12/125,544

(22) Filed: May 22, 2008

(65) Prior Publication Data

US 2008/0294172 A1 Nov. 27, 2008

(30) Foreign Application Priority Data

May 23, 2007 (DE) .................. 20 2007 007 322 U

(51) Int. Cl.
*A61B 17/17* (2006.01)

(52) U.S. Cl.
USPC .......................................... 606/96; 606/86 R

(58) Field of Classification Search ............ 606/99, 606/201–235, 96–98, 86 R; 623/17.11–17.16
See application file for complete search history.

(56) References Cited

U.S. PATENT DOCUMENTS

| | | | | |
|---|---|---|---|---|
| 5,584,887 A | * | 12/1996 | Kambin | 606/914 |
| 6,371,986 B1 | * | 4/2002 | Bagby | 623/17.11 |
| 2002/0165581 A1 | * | 11/2002 | Brucker | 606/213 |
| 2003/0083688 A1 | * | 5/2003 | Simonson | 606/191 |
| 2003/0233100 A1 | * | 12/2003 | Santarella et al. | 606/99 |
| 2004/0106997 A1 | * | 6/2004 | Lieberson | 623/17.16 |
| 2005/0256525 A1 | * | 11/2005 | Culbert et al. | 606/53 |
| 2005/0261698 A1 | * | 11/2005 | Powell | 606/96 |
| 2005/0283187 A1 | * | 12/2005 | Longson | 606/213 |
| 2006/0200160 A1 | | 9/2006 | Border et al. | |

FOREIGN PATENT DOCUMENTS

| | | |
|---|---|---|
| EP | 0617927 A1 | 10/1994 |
| EP | 1340467 A2 | 9/2003 |
| EP | 1743591 A2 | 1/2007 |
| WO | 0009024 A1 | 2/2000 |
| WO | 0160263 A1 | 8/2001 |

* cited by examiner

*Primary Examiner* — Kevin T Truong  
*Assistant Examiner* — Larry E Waggle, Jr.  
(74) *Attorney, Agent, or Firm* — Rothwell, Figg, Ernst & Manbeck, P.C.

(57) ABSTRACT

An instrument set for minimally invasive preparation for a bone nailing comprises at least one base sleeve (10) which has a selected axial length with a drive-in end and a tool working end (12) and an inner diameter selected for holding working sleeves (60) or a nail, in particular a medullary pin. Further, the instrument set comprises at least one substantially rigid guide wire (20) which has a selected diameter and a fixing tip (21) at one end, at least one dilation sleeve (30) which has an outer diameter adapted to the inner diameter of the base sleeve (10) for guided displacement therein, an end section (31) tapering away therefrom with an outlet opening (32) for the guided longitudinal displacement of the guide wire (20) through this, and a length which is greater than that of the base sleeve (10), and at least one working sleeve (60) which has an outer diameter adapted to the inner diameter of the base sleeve (10) or next largest working sleeve for guided displacement therein, a length which is greater than that of the base sleeve (10), an inner diameter adapted for guidance of a bore or cutter (90) or a nail to be inserted, and a stop (61) at its one end for working with the tool working end (12) of the base sleeve (10).

12 Claims, 3 Drawing Sheets

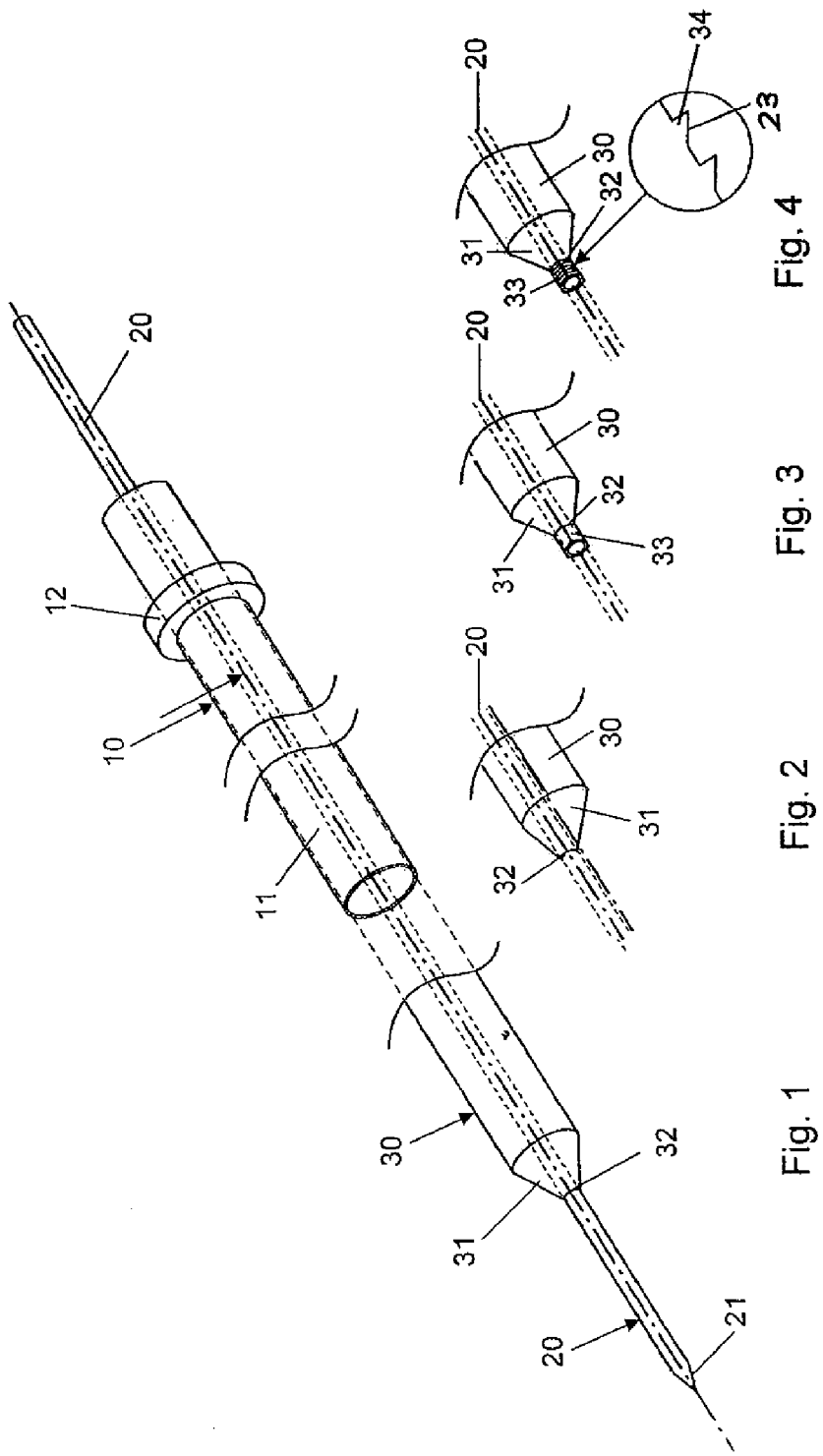

INSTRUMENT SET FOR MINIMALLY INVASIVE PREPARATION FOR BONE NAILING

CROSS REFERENCE TO RELATED APPLICATION(S)

Figure 5:
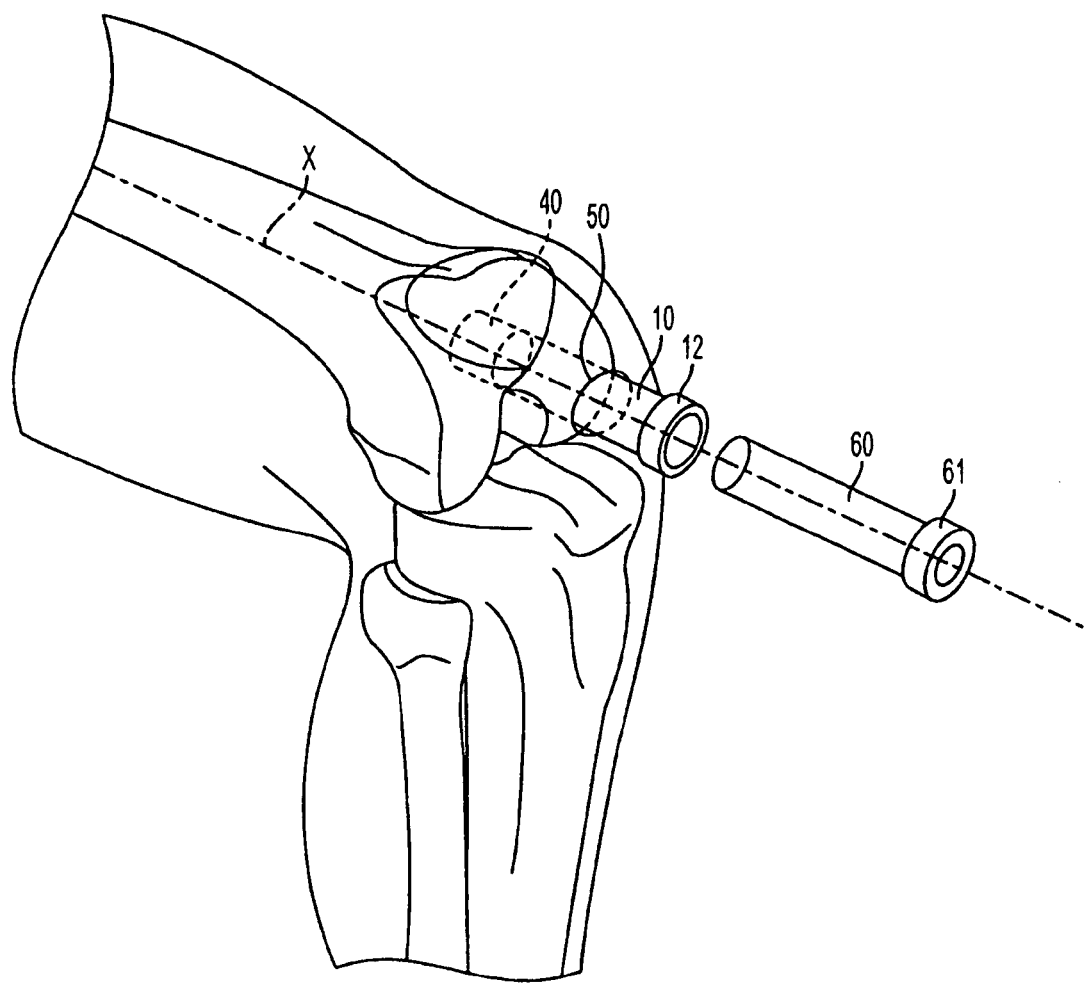

This application claims the benefit of German Patent Application No. 202007007322.4, filed May 23, 2007, the disclosure of which is incorporated herein in its entirety by reference.

The invention relates to an instrument set for minimally invasive preparation for bone nailing. The instrument set is intended primarily for minimally invasive preparation for bone nailing for the thigh, lower leg and upper arm bones. In principle it can however be used for minimally invasive preparation for nailing of other bones.

In the medical surgical sector, there is increasing demand for minimally invasive methods. This applies to both accident surgery and orthopaedics. One method established since the middle of the last century is bone nailing. Here a solid or internally hollow metal stabiliser is inserted in the medullary space of large tubular bones as an inner splint. Whereas previously major steps were required for this, increasingly effort is being made to develop minimally invasive operation techniques for this futuristic OP method, i.e. with minimum tissue damage.

The state of the art are individual implantation aids, e.g. trough-like or tubular tissue protection instruments which are fitted with a handle and can be used to protect soft tissue parts. With small calibre medullary pins which are used for preference in fracture treatment, for which no boring of the medullary space is required, operations can already be performed with minimum tissue damage.

For large calibre medullary pins which are advantageous in particular for secondary corrective measures but are also becoming increasingly important in fracture treatment, but in any case for medullary pins which require structuring of the medullary space, i.e. milling according to a plan and not following the path of least resistance, previously there has been no solution which meets current requirements.

Previously in medullary space milling, tissue protection was used in the form of a curved plate or a sleeve applied to the bone. These tools have numerous disadvantages. On proximal access to the femur for example the extracted material previously became distributed into the soft tissue parts and occasionally led to disruptive ossification. On distal access to the femur, the extracted material previously became distributed in the knee joint, which is also disadvantageous.

If for example a defective bone position is to be corrected and stabilised with a medullary pin, first the bone is cut operatively into a bone segment remote from the entrance and a bone segment close to the entrance, where there is not already a break in continuity. The milling of the bone segment remote from the entrance in the shaft centre, because of the usually hard diaphyseal bone structure, must usually take place in several successive milling processes. Since on each change, the cutters pass the bone segment close to the entrance and this passage, due to soft tissue, is often at an unfavourable angle, previously substantial correction losses occurred from secondary defective cutting in the bone segment close to the entrance.

The object on which the invention is based is to provide an instrument set with which as a whole it is possible to create a minimally invasive access route, during the entire process ensure extensive protection of soft tissue, prevent contamination by extracted material, precisely define the nail inlet point, precisely specify the milling direction and hence the nail direction, and ensure lining of the milling path of a bone segment close to the entrance of two bone segments to be joined by a nail.

This object is achieved by an instrument set for minimally invasive preparation for bone nailing with:
a) at least one base sleeve with a selected axial length, a drive-in end, a tool working end and an inner diameter selected for holding a working sleeve or nail, in particular a medullary pin,
b) at least one substantially rigid guide wire with a selected diameter and a fixing tip at one end,
c) at least one dilation sleeve with an outer diameter adapted to the inner diameter of the base sleeve for guided displacement therein and with an end section tapering away therefrom, which end section has an outlet opening for the guided longitudinal displacement of the guide wire through this, and with a length which is greater than that of the base sleeve, and
d) at least one working sleeve with an outer diameter adapted to the inner diameter of the base sleeve or next largest working sleeve for guided displacement therein, with a length which is greater than that of the base sleeve, with an inner diameter adapted for guidance of a bore or cutter or a medullary pin to be inserted, and with a stop at its one end for engagement with the tool working end of the base sleeve.

The end section of the dilation sleeve is advantageously a straight or inclined truncated circular cone or pyramid. When designed as an inclined truncated circular cone or pyramid, with controlled rotation of the dilation sleeve about the guide wire, a position correction of the base sleeve is possible by the amount by which the narrower end of the truncated circular cone or pyramid is designed eccentric.

Above all if the end section of the dilation sleeve is an inclined truncated circular cone or pyramid and a correction is achieved by rotating the dilation sleeve, due to soft tissue it has a tendency to return to the starting position. As the dilation sleeve cannot be fastened at the end, securing for the new twisted position must be provided. This is achieved by a fixing extension extended into the outlet opening, the inner diameter of which is dimensioned for a sliding seat with the guide wire and the outer surface of which in cross-section has the form of a polygon, for example a hexagon. If the fixing extension structured thus is impacted completely into the bone, the position of the dilation sleeve set by twisting is secured and retained even when the base sleeve is knocked in.

The reaction force occurring on knocking in the base sleeve has a tendency to drive back the dilation sleeve, whereby the bone contact and the position set by centring to the guide wire could be lost. In order to secure the outer polygon of the fixing extension in the bone against slipping out, there are advantageously provided on its outer surface locking projections substantially extending in the peripheral direction and spaced apart.

If the drive-side flanks of the locking projections are chamfered at their ends remote from the extension, pointing away from the drive side, it is easier to drive in the fixing extension and this cannot slip out so easily because of the hook-like effect.

The locking projections can be formed by thread turns or peripheral grooves lying in radial planes.

Suitably the tool working end of the base sleeve is a ring extending radially out therefrom, while the stop at the one end of the working sleeve can be a peripheral bead extending radially outwards.

The rigid guide wire suitably has a diameter of 2 to 5 mm, preferably 3 mm.

The base sleeve can have an inner diameter of 6 to 20 mm, a wall thickness of 1 to 3 mm and preferably comprise implant steel.

The instrument set can be supplemented by at least one knock-in instrument and/or an extraction tool for the base sleeve.

The outer diameter of the working sleeve is matched to the inner diameter of the base sleeve or the next largest working sleeve so that an axial sliding is possible. The inner diameter of the working sleeve is determined based on the drills or cutters to be guided therein and according to the outer diameter of the nail used, in particular the medullary pin. As required, several working sleeves of diameters adapted to each other and also of different lengths can be placed in one base sleeve.

For the working sleeves, several length stages are provided in order to allow the guided, stepped drilling of bone segments of different dimensions and subsequent precisely guided setting of the bone nail. The lengths of the base sleeves and dilation sleeves essentially depend on the thickness of the soft tissue parts to be penetrated.

The instrument set comprises, depending on requirements of the operator, around 20 to 100 sleeves.

Figure 6:
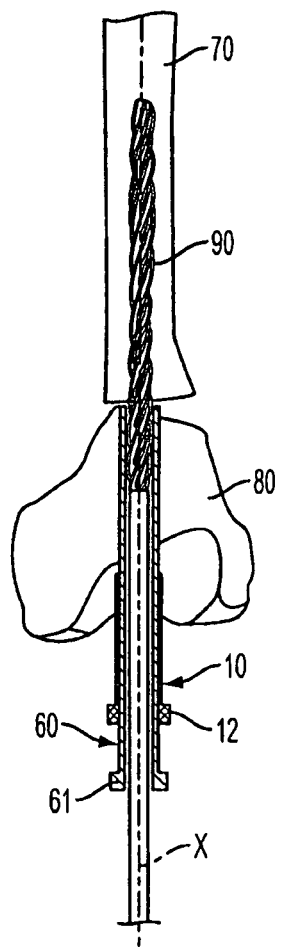

An example embodiment of the invention is described in more detail with reference to the drawings. These show:

FIG. 1 in perspective a base sleeve, a dilation sleeve and a guide wire of the instrument set, FIG. 2 in a view similar to FIG. 1, a dilation sleeve with an end section in the form of an inclined truncated circular cone, FIG. 3 in a view similar to FIG. 2, a dilation sleeve with an end section in the form of a straight truncated circular cone and with a smooth fixing extension on the tapered end of the end section of the dilation sleeve, FIG. 4 in a view similar to FIG. 3, the fixing extension with locking projections and the design of the locking projections in detail, FIG. 5 a perspective, exploded view of a base sleeve inserted in a femur from the distal end and a working sleeve for insertion in the base sleeve, and FIG. 6 diagrammatically in a partly cut-away view, two bone segments in which, using a base sleeve and working sleeves, only one of which is shown, an aligned bore is formed for subsequent insertion of a medullary pin.

FIG. 1 shows the central element of the instrument set comprising a thin-walled base sleeve 10 with a casing part 11 of steel, which at one end has an outwardly extending ring 12 for working with a tool. The instrument set can comprise several base sleeves 10 with internal diameters between 6 and 20 mm, wall thicknesses between 1 and 3 mm, and different usage-dependent lengths.

FIG. 1 shows a base sleeve 10 which is shown pushed over a dilation sleeve 30 of the instrument set. The dilation sleeve 30 has at one end a tapering end section 31 which ends in an outlet opening 32 formed for the guided passage of a guide wire 20 and with a tip 21.

The tapering end section 31 of the dilation sleeve 30 in the embodiment shown in FIG. 1 has the form of a straight truncated circular cone. In the embodiment in FIG. 2 the end section 31 has the form of an inclined truncated circular cone.

As FIG. 3 shows, applied to the tapered end of the end section 31 is a fixing extension 33 which has a passage aligned with the outlet opening 32 of the end section 31, with an inner diameter corresponding to the diameter of the outlet opening 32 and hence allowing the guided displacement of the guide wire 20. The outer surface of the fixing extension 33 in the embodiment shown forms a regular hexagon, also instead other polygonal profiles can be provided.

As FIG. 4 shows, the outer surface of the fixing extension 33 is fitted with locking projections which are designated by reference numeral 34 in the detail added in the circle in FIG. 4, and on the drive-in side have chamfered long flanks 23 which extend away from the drive-in side to their end remote from the extension, and return with a short flank to the outer surface of the fixing extension.

FIG. 5 shows a bone arrangement in which a base sleeve 10 is driven aligned along an axis X through a soft tissue passage 50 with a fixing section 40 into the bone. FIG. 5 further shows the insertion of a working sleeve 60 in the base sleeve 10, which in the fully introduced position (not shown) lies with an annular bead 61 on the face on the ring 12 of the base sleeve 10.

FIG. 6 shows two bone segments 70 and 80 which are aligned to each other along an axis X. In preparation for their joining by a nail not shown, in the bone segment 80 is fixed the base sleeve 10 through which a working sleeve 60 is arranged, through which in turn a drill 90 is guided so that it forms a bore in the bone segment 70 aligned to axis X, wherein the bone segment 80 is completely lined by the working sleeve 60 and hence protected.

The use of the instruments in the instrument set is described below as an example.

The positioning of the base sleeve 10 both with regard to position to the bone and with regard to alignment to the bone axis is of elementary importance. To determine the position exactly, the entrance point is established with a guide wire 20 with a tip 21 through the skin or via a mini-cut under an image converter. The guide wire 20 comprises a rigid material and usually has a diameter of 3 mm. When fixing the entrance point, the direction of running in the bone is initially of secondary importance.

The expansion of the soft tissue in the elastic range takes place via a dilation sleeve 30 which has an end section 31 tapering away from this to an outlet opening and which is pushed with its outlet opening over the guide wire 20 brought into position. The outer diameter of the dilation sleeve 30 and the inner diameter of the base sleeve 10 used are dimensioned so that the base sleeve 10 can be displaced under guidance on the dilation sleeve 30.

If the end section 31 is an inclined cone (FIG. 2), by twisting the dilation sleeve 30 the outer contour of the dilation sleeve 30 can be brought into any necessary correction position in relation to the guide wire 20 and hence the working sleeve 10, without the guide wire 20 having to be repositioned. Markings aligned to the end cone position are made on the outer free end of the dilation sleeve 30.

After fixing the entrance point using the guide wire 20 and after expanding the soft tissue using the dilation sleeve 30 pushed over the guide wire 20 and aligned for positioning of the base sleeve 10, the dilation sleeve 30 is fixed using its fixing extension 33 in that this is driven into the bone in which it is secured against twisting by its polygonal outer surface (FIG. 3) and against slipping out by its groove profile in FIG. 4. Then the base sleeve 10 is pushed over the dilation sleeve 30 and driven down to the bone, as shown in FIG. 5. Then with measured hammer blows using a tubular drift tool, it is impacted into the bone forming a fixing section 40, where in this process the planned milling direction is observed precisely. Depending on bone composition, to set a secure direction it is sufficient if the fixing section 40 is driven in to a depth of a few millimetres to one centimetre. Then the dilation sleeve 30 and the guide wire 20 are extracted.

To conclude this measure, the later medullary pin entrance point is determined and the course of all drills or cutters and hence of the later medullary pin is defined in the bone segment near the entrance. For this a single soft tissue passage 50 (FIG. 5) of the base sleeve 10 is required, which is achieved using the dilation sleeve 30, which is advantageous in terms of bacterial contamination. Also minor bleeding in the soft tissue is compressed. The entire extraction material occurring during the drilling and cutting process is passed to the outside and discharged through the base sleeve 10 impacted into the bone, which remains there for the entire preparation of the bone for the bone nailing.

Usually the bone—FIG. 6 shows for example a bone segment 80 close to the entrance and a bone segment 70 remote from the entrance—must be milled out concentrically in steps, starting with a small diameter. To allow a stepped reduction in internal diameter of the base sleeve 10 to the respective cutter diameter, the working sleeves 60 are provided which at their one end have the radially external annular stop or bead 61 for which the stop 12, extending radially outward from the base sleeve 10 in the form of a ring, serves as an abutment. The outer diameter of the working sleeve 60 is adapted to the inner diameter of the base sleeve 10 of the instrument set concerned so that each working sleeve 60 can be displaced under axial and radial guidance inside the associated base sleeve 10.

In particular if axis corrections are required, the cutting direction in the trumpet-like expansions of the bone ends must be produced precisely to the planning specifications (FIG. 6). Only then can the centre bone region be milled out. As the bone drill or cutter 90 for this must pass repeatedly through the bone segment 80 close to the entrance at an unfavourable angle, the use of correspondingly longer working sleeves 60 can serve as a splint for the bone segment 80 close to the entrance over its entire length, so that the cutters 90 have no contact here. By corresponding exchange of the working sleeves 60 with corresponding length and inner diameters adapted to the drills or cutters 90, a concentric milling out of the bone segment 70 remote from the entrance is guaranteed without a correction loss in the bone segment close to the entrance. Several working sleeves can also be placed inside each other. If the milling of the bone segment remote from the entrance takes place in several steps and at the same time it is necessary to line the bone segment close to the entrance for its protection, then one or more working sleeves of suitable diameter can be inserted into the arrangement as shown in FIG. 6, into the working sleeve 60, so that drills or cutters with smaller diameters can also be guided concentrically.

After removing the last drill 90 used, the minimally invasive preparation for bone nailing is complete. Now a medullary pin not shown can be placed through the base sleeve into the aligned bores in the bone segment 80 close to the entrance and in the bone segment 70 remote from the entrance, in the correct position. The base sleeve is then removed.

The base sleeve can however also be removed after completion of the preparation for bone nailing so that the medullary pin can then be positioned directly in the aligned bone bores.

The invention claimed is:

1. Instrument set for minimally invasive preparation for a bone nailing, comprising:
   a) at least one base sleeve which has
      a selected axial length with a drive-in end and a tool working end and
      an inner diameter selected for holding working sleeves or a nail;
   b) at least one substantially rigid guide wire which has
      a selected diameter and
      a fixing tip at one end;
   c) at least one dilation sleeve which has
      an outer diameter adapted to the inner diameter of the base sleeve for guided displacement therein,
      an end section tapering away therefrom with an outlet opening for the guided longitudinal displacement of the guide wire through this, and
      a length which is greater than that of the base sleeve;
   d) at least one working sleeve which has
      an outer diameter adapted to the inner diameter of the base sleeve or a next largest working sleeve for guided displacement therein,
      a length which is greater than that of the base sleeve,
      an inner diameter adapted for guidance of a drill or cutter or a nail to be inserted, and
      a stop at its one end for engaging with the tool working end of the base sleeve; and
   e) a fixing extension extending the outlet opening of the dilation sleeve, the inner diameter of which is dimensioned for a sliding seat with the guide wire and the outer surface of which has a polygonal cross-section.

2. Instrument set according to claim 1, wherein the end section of the dilation sleeve is a straight or inclined truncated circular cone or pyramid.

3. Instrument set according to claim 1, further comprising locking projections extending substantially in the peripheral direction and spaced apart from each other on the outer surface of the fixing extension.

4. Instrument set according to claim 3, wherein the locking projections have flanks on a drive-in side which are chamfered at their ends remote from the extension pointing away from the drive-in side.

5. Instrument set according to claim 3, wherein the locking projections are formed by thread turns or by peripheral grooves lying in radial planes.

6. Instrument set according to claim 1, wherein the tool working end of the base sleeve is formed by a radially outwardly extending ring.

7. Instrument set according to claim 1, wherein the stop at the one end of the working sleeve is formed by a radially outwardly extending peripheral bead.

8. Instrument set according to claim 1, wherein the guide wire has a diameter of 2 to 5 mm, preferably 3 mm.

9. Instrument set according to claim 1, wherein the base sleeve has an inner diameter of 6 to 20 mm.

10. Instrument set according to claim 1, wherein the wall thickness of the base sleeve is 0.5 to 3 mm.

11. Instrument set according to claim 1, wherein the base sleeve comprises implant steel.

12. Instrument set according to claim 1, wherein in addition at least one knock-in instrument and/or extraction tool for the base sleeve is provided.

* * * * *